(12) United States Patent
Dy et al.

(10) Patent No.: US 6,283,943 B1
(45) Date of Patent: *Sep. 4, 2001

(54) NEGATIVE PRESSURE PUMP

(75) Inventors: Norman Dy, Burbank; William P. Van Antwerp, Valencia, both of CA (US)

(73) Assignee: MiniMed Inc., Northridge, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/253,383

(22) Filed: Feb. 19, 1999

(51) Int. Cl.[7] ................................................. A61M 37/00
(52) U.S. Cl. ......................... 604/141; 604/891.1; 604/505
(58) Field of Search ..................... 604/891.1, 890.1, 604/93, 132, 140, 141, 142, 502, 505; 128/DIG. 12

(56) References Cited

U.S. PATENT DOCUMENTS

| | | | |
|---|---|---|---|
| 3,692,027 | * | 9/1972 | Ellinwood, Jr. . |
| 3,731,681 | * | 5/1973 | Blackshear et al. . |
| 3,788,322 | * | 1/1974 | Michaels . |
| 3,797,492 | * | 3/1974 | Place . |
| 4,140,122 | * | 2/1979 | Kuhl et al. . |
| 4,191,181 | * | 3/1980 | Franetzki et al. . |
| 4,258,711 | * | 3/1981 | Tucker et al. . |
| 4,573,994 | | 3/1986 | Fischell et al. . |
| 4,619,653 | * | 10/1986 | Fischell . |
| 4,655,765 | | 4/1987 | Swift . |
| 4,667,855 | * | 5/1987 | Holleran . |
| 4,668,231 | * | 5/1987 | De Vries et al. ................ 604/891.1 |
| 4,820,273 | * | 4/1989 | Reinicke ................ 604/141 |
| 4,969,873 | * | 11/1990 | Steinbach et al. ................ 604/93 |
| 5,085,656 | * | 2/1992 | Polashegg ................ 604/891.1 |
| 5,167,633 | * | 12/1992 | Mann et al. ................ 604/141 |
| 5,318,540 | * | 6/1994 | Athayde et al. ................ 604/141 |
| 5,382,236 | * | 1/1995 | Otto et al. ................ 604/141 |
| 5,466,218 | * | 11/1995 | Srisathapat et al. ................ 604/49 |
| 5,514,103 | | 5/1996 | Srisathapat et al. . |
| 5,607,418 | * | 3/1997 | Arzbaecher ................ 604/891.1 |
| 5,667,504 | * | 9/1997 | Baumann et al. ................ 604/891.1 |
| 5,722,957 | * | 3/1998 | Steinbach ................ 604/141 |
| 5,766,150 | * | 6/1998 | Langkau ................ 604/93 |
| 5,769,823 | * | 6/1998 | Otto ................ 604/141 |
| 5,785,688 | * | 7/1998 | Joshi et al. ................ 604/141 |
| 5,814,019 | * | 9/1998 | Steinbach et al. ................ 604/131 |
| 5,908,414 | * | 6/1999 | Otto et al. ................ 604/891.1 |
| 5,957,890 | * | 9/1999 | Mann et al. ................ 604/131 |

FOREIGN PATENT DOCUMENTS 0 488 701 A1   6/1992 (EP) .
WO 97/40873  11/1997 (WO) .

OTHER PUBLICATIONS

Hawley, Gessner Goodrich, "Hawley's Condensed Chemical Dictionary: Thirteenth edition," John Wiley & Sons, Inc. (see attached pages), 1997.*

* cited by examiner

Primary Examiner—Anhtuan T. Nguyen
Assistant Examiner—Michael M. Thompson
(74) Attorney, Agent, or Firm—Gates & Cooper LLP

(57) ABSTRACT

A medication infusion pump includes a housing, a medication chamber defined within the housing, means for supplying the medication from the medication chamber to a patient, a reservoir defined within the housing and adapted to apply a predetermined negative pressure to a medication within the medication chamber, and a gas within the reservoir. The gas has a vapor pressure less than ambient atmospheric pressure at normal human physiological temperature, more specifically less than 14.7 psia at 37° C.

18 Claims, 2 Drawing Sheets

NEGATIVE PRESSURE PUMP

FIELD OF THE INVENTION

The present invention relates to medication infusion pumps, more particularly implantable infusion pumps.

BACKGROUND OF THE INVENTION

Medication infusion pumps that supply a medication to a patient, in particular implantable infusion pumps, are known. Known infusion pumps typically include a housing that contains a medication chamber and a propellant chamber, together with appropriate means for loading the selected medication into the medication chamber and for supplying the medication to the patient. One known type of infusion pump includes a reservoir containing a gas at a pressure below atmospheric pressure. Such infusion pumps are characterized as "negative pressure" pumps. Negative pressure pumps offer the advantage of facilitating fill of the medication chamber by acting to draw in the medication from a hypodermic needle or other supply source into the medication chamber. Such pumps also have the advantage of inhibiting undesirable leakage from the medication chamber.

Negative pressure infusion pumps are described, for example, in U.S. Pat. No. 4,191,181, to Frenetzki et al.; U.S. Pat. No. 4,373,527, to Fischell; U.S. Pat. No. 4,511,355, to Frenetzki et al.; U.S. Pat. No. 4,573,994, to Fischell et al.; and U.S. Pat. No. 5,514,103, to Srisathapat et al. In a typical negative pressure infusion pump, a medication is drawn into the medication chamber under the action of a gas maintained in a flexible reservoir at negative pressure. Once the medication is drawn into the medication chamber, the medication is subsequently delivered to the patient via a separate pumping mechanism.

Modern environmental concerns mandate that gases employed in "negative pressure" pumps be environmentally benign. It is of particular concern to avoid gases that have an adverse effect on ozone.

A need exists for a negative pressure infusion pump that employs an environmentally acceptable gas in its gas reservoir.

SUMMARY OF THE PREFERRED EMBODIMENTS

In accordance with one aspect of the present invention, there is provided a medication infusion pump that includes a housing, a medication chamber defined in the housing, a pumping mechanism for supplying the medication from the medication chamber to a patient, a reservoir defined in the housing and adapted to apply a predetermined negative pressure to a medication within the medication chamber, and a gas within the reservoir. The gas has a vapor pressure less than ambient atmospheric pressure at 37° C., more particularly less than 14.7 psia at 37° C.

The gas is preferably a non-ozone depleting, non-toxic gas.

In a preferred embodiment, the propellant is a gas selected from the group consisting of cyclopentane and dimethylbutane.

In accordance with another aspect of the present invention, there is provided a medication infusion pump adapted to be passively refilled with a medication. The medication infusion pump includes a reservoir that contains a gas having a vapor pressure less than ambient atmospheric pressure at 37° C., more particularly less than 14.7 psia at 37° C.

In accordance with another aspect of the present invention, there is provided a method of supplying a medication to a patient from an infusion pump as described herein. The method includes the steps of filling said reservoir with a propellant having a vapor pressure less than ambient atmospheric pressure at 37° C., drawing the medication into the medication chamber by exertion of the predetermined negative pressure on the medication, and dispensing the medication from the medication chamber via a pumping mechanism.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

The invention may be more readily understood by referring to the accompanying drawings in which.

DETAILED DESCRIPTION OF THE PREFERRED EMBODIMENTS

Figure 1:
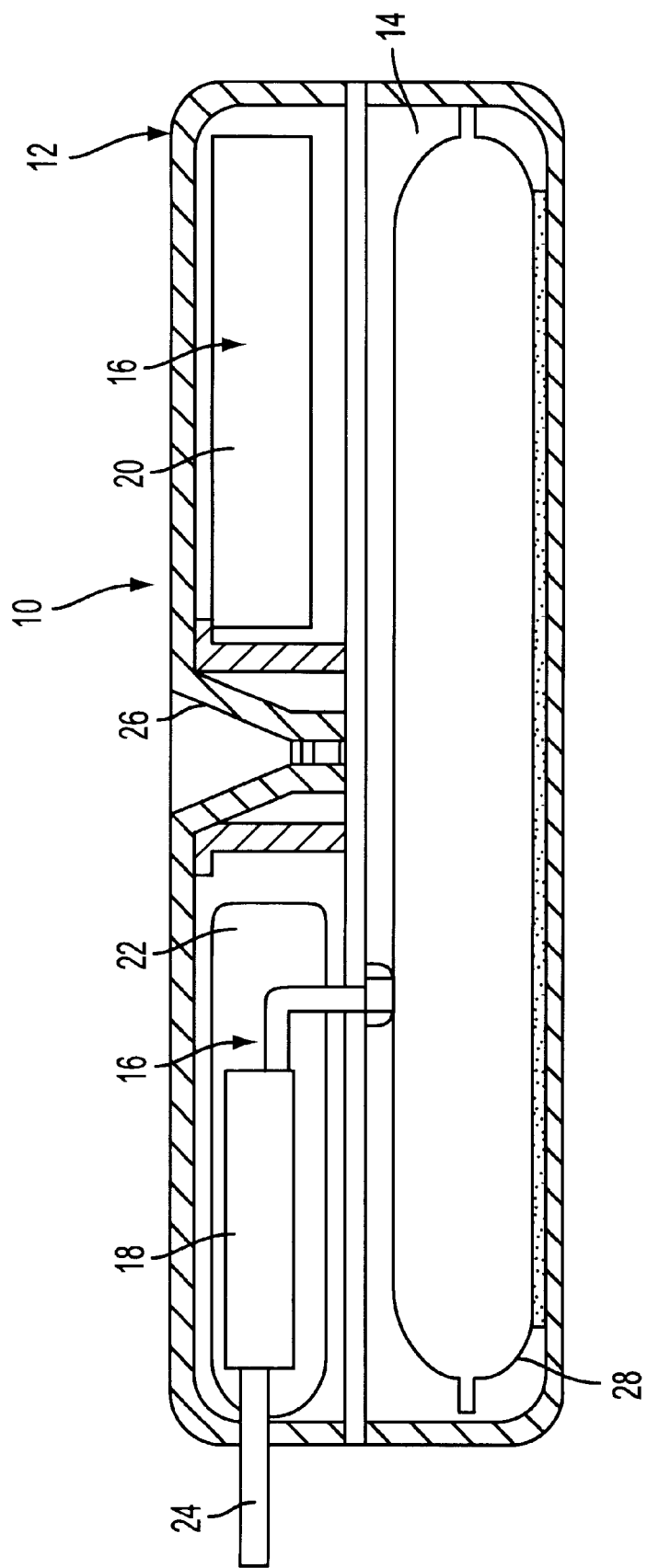
FIG. 1 is a side sectional view of a negative pressure medication infusion pump according to the present invention that employs a flexible bladder as the gas reservoir.

Gases are "non-toxic" for the purposes of this invention if they comply with the standard established in ISO 10993. Gases are also "non-toxic" for the purposes of this invention if they are included in the inventory of the Toxic Substances Control Act.

A gas is considered "non-ozone depleting" for the purposes of this invention if (i) the gas has an Ozone Depletion Potential (ODP) less than 1.0, more preferably less than about 0.10 (with the ODP of CFC-11=1.0) and either (ii) the gas is not a Class I or Class II controlled substance as set forth in 40 C.F.R. Part 82, Subpart A, or (iii) the gas is subject to the exemption provided for under 40 C.F.R. §82.4(s)(1) (use in a medical device). Determination of the ODP of a gas is readily carried out by those skilled in the art.

Gases useful according to the present invention have a vapor pressure less than ambient atmospheric pressure at normal human physiological temperature (37° C.). More particularly, the gas has a vapor pressure less than sea level atmospheric pressure (14.7 psia) at 37° C. Preferably, the gas has a vapor pressure less than 10.7 psia at 37° C. Exemplary gases include cyclopentane (vapor pressure 9.4 psia at 37° C.) and 2,2-dimethylbutane (vapor pressure 9.6 psia at 37° C.). Other useful gases include 1,3-pentadiene (vapor pressure 12.50 at 37° C.), 2-methyl-2-butene (vapor pressure 14.24 psia at 37° C.), and methyl iodide (vapor pressure 11.10 psia at 37° C.). Other branched chain fluoroalkanes and fluoroalkenes are also suitable for use according to the instant invention.

Gases having vapor pressures lower than 10.7 psia at 37° C. are particularly desirable in that infusion pumps that employ such gases can be effectively used even at relatively high altitudes. For example, the vapor pressure of 2,2-dimethylbutane, 9.4 psia, corresponds to an altitude of about 12,000 feet above sea level. The vapor pressure of cyclopentane, 9.6 psia, corresponds to an altitude of about 11,500 feet. Thus, use of the foregoing preferred gases in accordance with the present invention allows the inventive infusion pump to be employed in almost all major population centers and most mountain areas, as well as in aircraft. When implanted in a human patient, these embodiments of the inventive infusion pump allow the patient to travel freely.

It is also contemplated that mixture of two or more gases are also useful according to the instant invention, provided that the mixture is capable of maintaining a pressure less than 14.7 psia, more preferably less than 10.7 psia.

Desirably, the gas or gas mixture maintains the reservoir at a pressure less than 14.7 psia, more preferably less than 10.7 psia, at 37° C. when the medication chamber is filled and also when the medication is unfilled.

Turning now to FIG. 1, a schematic representation of a first embodiment of a medication infusion pump 10 according to the invention includes a housing 12 within which a medication chamber 14 is defined. A pumping mechanism 16 is provided for supplying a medication from medication chamber 14 to a patient. The pumping mechanism 16 include a pump 18, control circuitry 20, battery 22 and catheter 24. Other known means for supplying a medication from medication chamber 14 can also be employed.

A medication is loaded into medication chamber 14, for example, via an inlet or refill fitting 26 adapted to receive a hypodermic needle (not shown).

Reservoir 28 is defined within housing 12. In the illustrated embodiment, reservoir 28 is a flexible and expansible bag formed from a polymeric material and secured within housing 12. Alternatively, reservoir 28 can be defined by a flexible membrane that extends across the interior of housing 12. The selected gas or gas mixture is supplied to reservoir 28 at the selected pressure by conventional means known to those skilled in the art.

A medication is loaded into medication chamber 14, for example, via an inlet or refill fitting 26 adapted to receive a hypodermic needle (not shown). Due to the negative pressure maintained in reservoir 22, the medication is passively drawn into the medication chamber 14, and is subsequently dispensed via pump 18.

Figure 2:
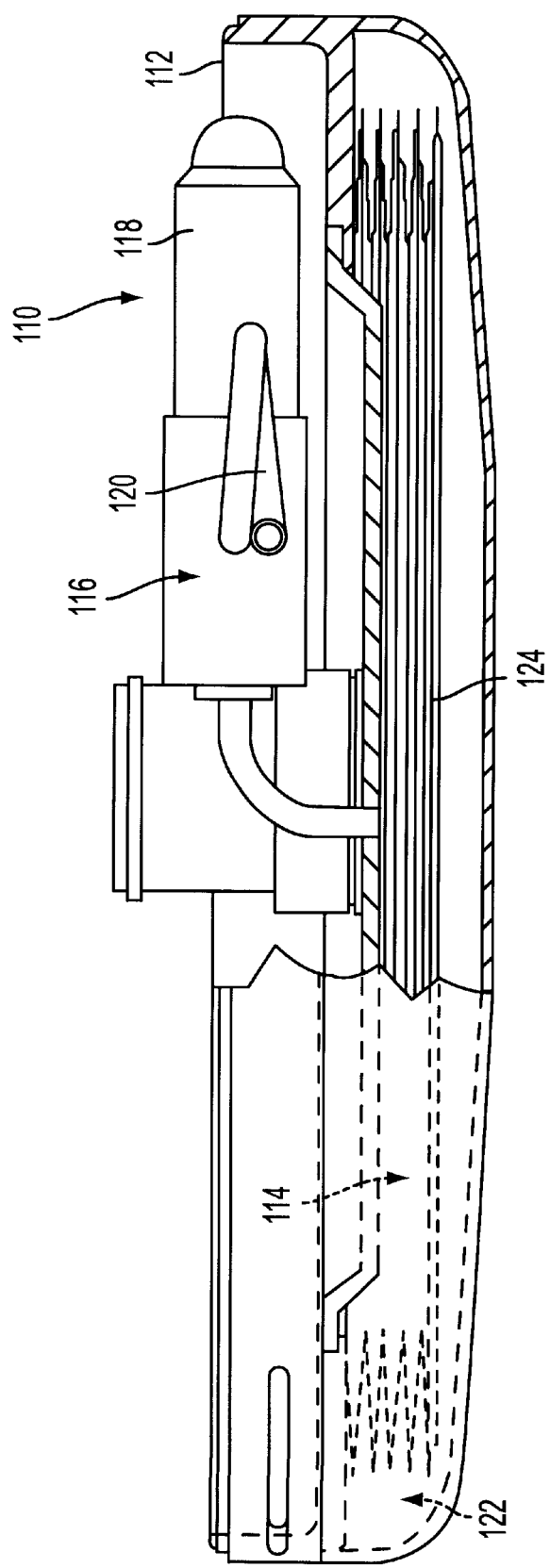
FIG. 2 is a schematic representation, partially cut-away, of a portion of an alternative embodiment of a negative pressure medication infusion pump according to the present invention that employs a corrugated gas reservoir.

In FIG. 2, an alternative embodiment of a medication infusion pump 110 according to the invention employs a reservoir defined by a flexible corrugated structure. Housing 112 has defined therein medication chamber 114. Pumping mechanism 116 for supplying the medication from medication chamber 114 to a patient includes pump 118, control circuitry and battery (not shown), and catheter 120.

Reservoir 122 is defined within housing 112 and is separated from medication chamber 114 by flexible corrugated structure 124. Structure 124 is preferably formed from a corrugated metal, for example titanium. The material used to form structure 124 again preferably is substantially impermeable to the gas mixture, the selected medication, and any gases dissolved in the medication. The selected gas or gas mixture is supplied to reservoir 122 by conventional means known to those skilled in the art.

What is claimed is:

1. A method of inhibiting undesirable leakage from a medication infusion pump comprising employing a non-ozone depleting gas having a vapor pressure less than ambient atmospheric pressure at 37° C. within the medication infusion pump, wherein the medication infusion pump comprises:
   a) a housing,
   b) a medication chamber defined within the housing,
   c) means for supplying the medication from the medication chamber to a patient,
   d) a reservoir defined within the housing and adapted to apply a predetermined negative pressure to the medication chamber; and
   e) the non-ozone depleting gas within the reservoir, wherein the gas has a vapor pressure less than ambient atmospheric pressure at normal human physiological temperature;
   wherein the vapor pressure of the gas applies a negative pressure to the medication chamber so that undesirable leakage is inhibited and wherein the method of inhibiting undesirable leakage from a medication infusion pump comprising employing a non-ozone depleting gas in said medication infusion pump further functions to avoid depletion of the ozone layer.

2. The method of claim 1 wherein the gas is non toxic.

3. The method of claim 1 wherein the gas has a vapor pressure less than 14.7 psia at 37° C.

4. The method of claim 3 wherein the gas has a vapor pressure less than 10.7 psia at 37° C.

5. The method of claim 1 wherein the gas is selected from the group consisting of cyclopentane, 2,2-dimethylbutane, 1,3-pentadiene and 2-methyl-2-butene.

6. The method of claim 5 wherein the gas is selected from the group consisting of cyclopentane and dimethylbutane.

7. The medication infusion pump of claim 1 comprising a plurality of gases within the reservoir, wherein the plurality of gases has a combined vapor pressure less than 14.7 psia at 37° C.

8. The method of claim 1 wherein the medication chamber and the reservoir are separated by a barrier which is resistant to the gas.

9. A method of facilitating the introduction of a medication into a medication chamber within a medication infusion pump comprising employing a non-ozone depleting gas having a vapor pressure less than ambient atmospheric pressure at 37° C. within the medication infusion pump, wherein the medication infusion pump comprises:
   a) a housing,
   b) a medication chamber defined within the housing,
   c) means for supplying the medication from the medication chamber to a patient,
   d) a reservoir defined within the housing and adapted to apply a predetermined negative pressure to the medication chamber; and
   e) the non-ozone depleting gas within the reservoir, wherein the gas has a vapor pressure less than ambient atmospheric pressure at normal human physiological temperature;
   wherein the vapor pressure of the gas applies a negative pressure to the medication chamber that facilitates the flow of the medication from a supply source into the medication chamber and wherein the method of facilitating the introduction of a medication into a medication chamber within a medication infusion pump comprising employing a non-ozone depleting gas in said medication infusion pump further functions to avoid depletion of the ozone layer.

10. The method of 9 wherein the gas is non toxic.

11. The method of claim 9, wherein the gas has a vapor pressure less than 14.7 psia at 37° C.

12. The method of claim 9 wherein the gas has a vapor pressure less than 10.7 psia at 37° C.

13. The method of claim 9 wherein the gas is selected from the group consisting of cyclopentane, 2,2-dimethylbutane, 1,3-pentadiene and 2-methyl-2-butene.

14. The method of claim 13 wherein the gas is selected from the group consisting of cyclopentane and dimethylbutane.

15. The medication infusion pump of claim 9 comprising a plurality of gases within the reservoir, wherein the plurality of gases has a combined vapor pressure less than 14.7 psia at 37° C.

16. The method of claim 9 wherein the medication chamber and the reservoir are separated by a barrier which is resistant to the gas.

17. A method of avoiding depletion of the ozone layer comprising using a non-ozone depleting gas having a vapor pressure less than ambient atmospheric pressure at 37° C. to inhibit a substance from escaping from the interior of a medication infusion pump to the exterior environment, wherein the medication infusion pump comprises:

a) a housing, b) a medication chamber defined within the housing, c) means for supplying the medication from the medication chamber to a patient, d) a reservoir defined within the housing and adapted to apply a predetermined negative pressure to the medication chamber; and e) the non-ozone depleting gas within the reservoir, wherein the gas has a vapor pressure less than ambient atmospheric pressure at normal human physiological temperature; and wherein the vapor pressure of the gas applies a negative pressure to the medication chamber that inhibits a substance from escaping from the interior of a medication infusion pump to the exterior environment.

18. A method of avoiding depletion of the ozone layer comprising using a non-ozone depleting gas having a vapor pressure less than ambient atmospheric pressure at 37° C. to facilitate the introduction of a medication into a medication chamber within a medication infusion pump, wherein the medication infusion pump comprises:

a) a housing, b) the medication chamber defined within the housing, c) means for supplying the medication from the medication chamber to a patient, d) a reservoir defined within the housing and adapted to apply a predetermined negative pressure to the medication chamber, and e) the non-ozone depleting gas within the reservoir, wherein the gas has a vapor pressure less than ambient atmospheric pressure at normal human physiological temperature; and wherein the vapor pressure of the gas applies a negative pressure to the medication chamber that facilitates the flow of the medication from a supply source into the medication chamber.

* * * * *